Jan. 1, 1974 R. KORDES Plant Pat. 3,414
ROSE PLANT
Filed Nov. 22, 1971
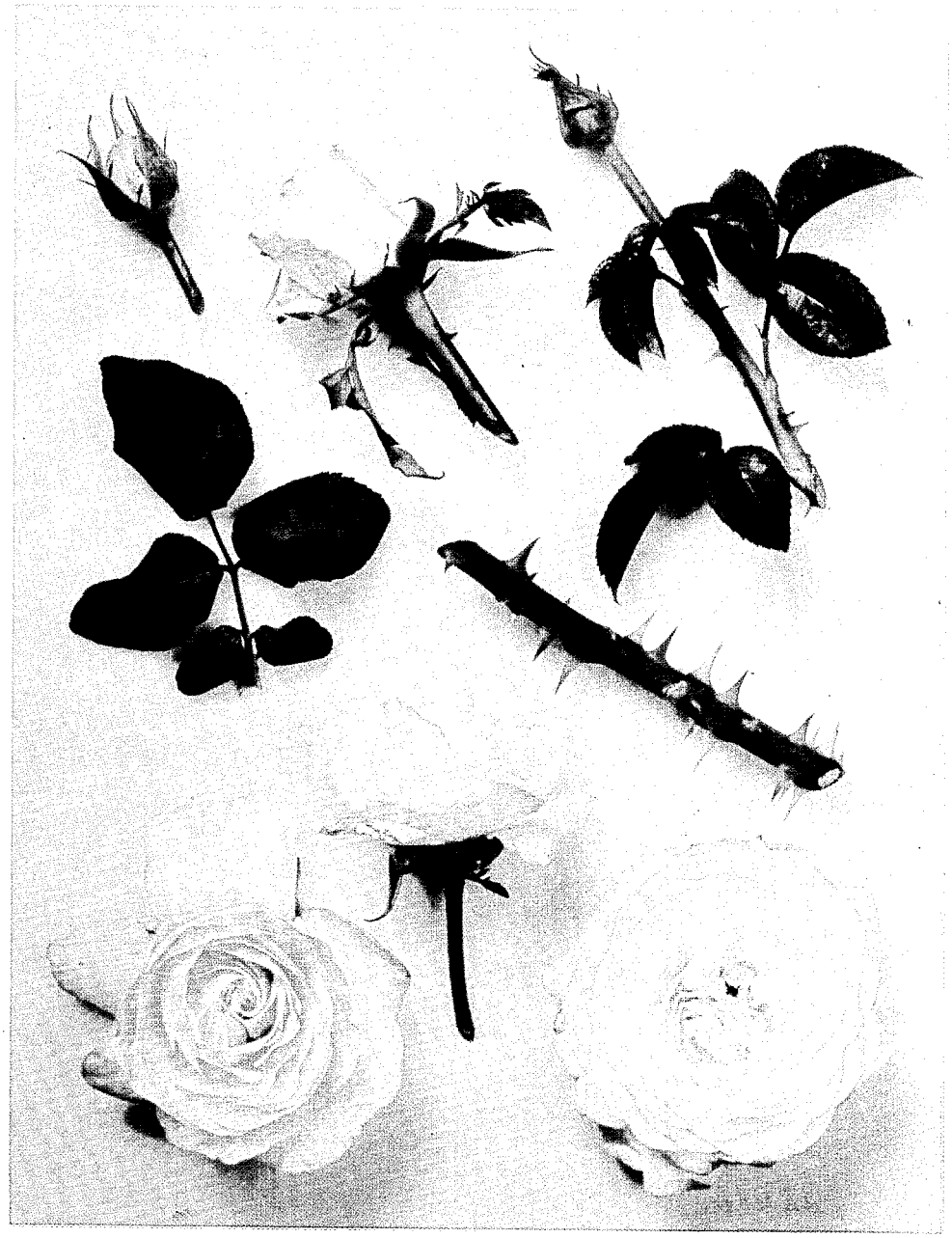
REIMER KORDES
INVENTOR
BUCKHORN, BLORE, KLARQUIST & SPARKMAN
ATTORNEYS United States Patent Office Plant Pat. 3,414
Patented Jan. 1, 1974

3,414
ROSE PLANT

Reimer Kordes, Sparrieshoop, near Elmshorn, Germany, assignor to Jackson & Perkins Company, Medford, Oreg.

Filed Nov. 22, 1971, Ser. No. 201,217
Int. Cl. A01h 5/00
U.S. Cl. Plt.—15 1 Claim This invention relates to a new and distinct variety of rose plant of the hybrid tea class originated by me by crossing the variety Konigin der Rosen with the variety Golden Wave, U.S. Plant Pat. 2,105.

The primary objective of this breeding was to produce a new and improved variety of the hybrid tea class which would have large blooms in the yellow range carried on compact, erect, strong stemmed plants.

This objective was fully achieved along with other desirable improvements as evidenced by the following unique combination of characteristics which are outstanding in the new variety and which distinguish it from its parents as well as from all other varieties of which I am aware:

(1) An erect type of plant whose canes and flower stems carry the blooms in an upright manner.
(2) Large flower, often 5½ inches in diameter when open, having 45 to 50 petals.
(3) Unusually thick petals for a very double variety.
(4) A rich Lemon yellow flower slightly overlaid with Neyron rose and Nasturtium Orange in its early stages.

Asexual reproduction of this new variety by budding as performed at Sparrieshoop, Holstein, Germany, shows that the aforementioned characteristics come true to form, and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of the new rose variety, with color terminology in accordance with Wilson's Horticultural Color Chart, except when ordinary dictionary meaning is indicated.

Parentage: Seedling
*Seed parent.*—Konigin der Rosen.
*Pollen parent.*—Golden Wave, U.S. Plant Patent 2,105.

Classification:
*Botanic.*—Rosa hybrid.
*Commercial.*—Hybrid tea.

FLOWER (Observations were made in early October at Irvine, Calif.)

Blooming habit: Recurrent—continuous.

Bud:
*Size.*—1¼–1⅜ inches when petals start to unfurl.
*Form.*—Short, pointed, ovoid, broad based.
*Color.*—When sepals first divide—Chinese yellow (606), except where first exposed to light, here overlaid with irregular areas of Neyron Rose (623) and Delft Rose (020), Petal tips often lighty tinted with Neyron Rose (623). When half blown—inside of petals near Lemon yellow (4) lightly overlaid with Nasturtium Orange (610); reverse of petals near Lemon yellow (4/1) with very little overlay of Nasturtium Orange.
*Sepals.*—Color: Outside: Scheeles Green (860/3) streaked on exposed side with Oxblood Red (00823/3). Surface scattered with gland tipped hairs. Inside: Near but much lighter than Garnet Brown (00918/3) covered with white tomentum. Three appendaged sepals normally appendaged. Two unappendaged sepals smooth edged.
*Receptacle.*—Color: Lettuce Green (861/1). Shape: Very broadly conical. Size: Large, broad. Surface: Smooth.
*Peduncle.*—Length: Medium. Surface: Prickly. Color: Lettuce Green (861/1) on shady side, Garnet Brown (00918/3) on sunny side. Strength: Stiff, erect.
*Opening.*—Petals remain nearly flat as they fold out.

Bloom:
*Size.*—Large (4" to 5½").
*Borne.*—Singly.
*Stems.*—Medium.
*Form.*—When first open—high center. Permanence—retains its form to the end. Reproductive parts exposed in very open form.
*Petalage.*—From 45 to 50.
*Color.*—Center of flower: Upper side of petals—Lemon Yellow (4/1). Reverse side of petals—Lemon Yellow (4/2). Outer petals: Upper side of petals—Lemon Yellow (4) at base fading to Lemon Yellow (4/3) at outer tip. Reverse of petals: Aureolin (3) at base fading to Aureolin (3/3) at outer tip. Base of petals: Lemon Yellow (4). General tonality from a distance—Lemon Yellow (4).
*Discoloration.*—General tonality at end of first day—same. Third day—Center petals Lemon Yellow (4/1). Outer petals Lemon Yellow (4/2).
*Fragrance.*—Slight.

Petals:
*Texture.*—Thick.
*Surface.*—Inside—satiny. Reverse—satiny.
*Shape.*—Round.
*Form.*—Slightly curved from base to tip with sides very little curled down.
*Arrangement.*—Imbricated.
*Persistance.*—Drop off cleanly.
*Lastingness.*—On the plant—long. As cut flower—long.

Reproductive parts:
*Stamens, anthers.*—Medium. Color—yellow. Arrangement—regular around styles, mixed with petaloids.
*Stamens, filaments (threads).*—Long—medium. Color—yellow.
*Pollen.*—Lemon Yellow.
*Styles.*—Loosely separated.
*Stigmas.*—Color—yellow.
*Ovaries.*—All enclosed in calyx.

PLANT

Form: Bush.

Growth: Very vigorous; upright. Flowering stems are unusually strong and erect.

Foliage: Compound of 5 leaflets.
*Size.*—Medium.
*Quantity.*—Normal.
*Color.*—New foliage: Near Garnet brown (00918/3). Old foliage: Close to Parsley green (00962).
*Leaflets.*—Shape—Oval. Texture—Upper side, leathery. Under side, smooth. Ribs and veins, ordinary. Edge—Serrated. Serration—Small, irregular or uneven. Petiole—Rachis—Color, green. Underside—prickles. Stipules—Long. Disease resistance—Resistant to mildew under normal growing conditions at Irvine, Calif.

Wood:

*New wood.*—Color—Light green. Bark—smooth.

*Old wood.*—Color—Green. Bark—smooth.

Prickles:

*Quantity.*—On main stalks—many. On laterals—many.

*Form.*—Straight.

*Color.*—Brown.

*Short prickles.*—Quantity: On main stalks—few. On laterals—few.

I claim:

1. A new and distinct variety of rose plant of the hybrid tea class, substantially as herein shown and described, characterized particularly as to novelty by the combination of a very double, large flower of Lemon yellow, overlaid in early stages by Neyron rose and Nasturtium orange, borne on stiff, erect, thorny stems.

No references cited.

ROBERT E. BAGWILL, Primary Examiner